(12) United States Patent
Jarvis

(10) Patent No.: US 9,710,564 B2
(45) Date of Patent: *Jul. 18, 2017

(54) PROVIDING LOCATION AND SPATIAL DATA ABOUT THE PHYSICAL ENVIRONMENT

(71) Applicant: International Business Machines Corporation, Armonk, NY (US)

(72) Inventor: Matthew J. Jarvis, Manchester (GB)

(73) Assignee: International Business Machines Corporation, Armonk, NY (US)

( * ) Notice: Subject to any disclaimer, the term of this patent is extended or adjusted under 35 U.S.C. 154(b) by 247 days.

This patent is subject to a terminal disclaimer.

(21) Appl. No.: 13/905,610

(22) Filed: May 30, 2013

(65) Prior Publication Data

US 2013/0332452 A1    Dec. 12, 2013

(30) Foreign Application Priority Data

May 30, 2012   (GB) .................................. 1209585.7

(51) Int. Cl.
   *G06F 17/30*    (2006.01)
   *G09B 21/00*    (2006.01)
   (Continued)

(52) U.S. Cl.
   CPC ......... *G06F 17/3087* (2013.01); *A61H 3/061* (2013.01); *G01S 5/02* (2013.01);
   (Continued)

(58) Field of Classification Search
   CPC combination set(s) only.
   See application file for complete search history.

(56) References Cited

U.S. PATENT DOCUMENTS 6,992,592 B2   1/2006  Gilfix et al.
7,267,281 B2   9/2007  Hopkins
               (Continued)

FOREIGN PATENT DOCUMENTS

CN    201912401    8/2011
FR      2945635   11/2010
              (Continued)

OTHER PUBLICATIONS

Kanbara et al., Registration for Stereo vision-based augmented reality based on extendible tracking of markers and natural features, 2002, vol. 2, IEEE, 1045-1048.*

(Continued)

*Primary Examiner* — Taelor Kim
(74) *Attorney, Agent, or Firm* — Yee & Associates, P.C.; Grant Johnson

(57) ABSTRACT

A system and computer program product are provided for providing location and spatial data about the physical environment. The system is configured to sense a tag provided in the environment by a mobile device; receive data from the tag at the mobile device, the data including location and spatial data relating to the physical environment of the tag; and represent the location and spatial data from the tag by the mobile device. In one embodiment, sensing a tag may include sensing a tag in the form of a machine-readable symbol; and receiving data from the tag receives data by processing an image of the machine-readable symbol by the mobile device. In another embodiment, sensing a tag includes sensing a tag in the form of a transmitter device; and receiving data from the tag receives data by receiving a signal by the mobile device.

12 Claims, 8 Drawing Sheets

(51) Int. Cl.
*A61H 3/06* (2006.01)
*G01S 5/02* (2010.01)
*G01S 5/16* (2006.01)
*G06F 3/00* (2006.01)
*G06F 3/01* (2006.01)
*A61F 9/08* (2006.01)

(52) U.S. Cl.
CPC ............ *G01S 5/0263* (2013.01); *G01S 5/16*
(2013.01); *G06F 3/005* (2013.01); *G06F*
*3/016* (2013.01); *G09B 21/003* (2013.01);
*G09B 21/006* (2013.01); *G09B 21/007*
(2013.01); *G09B 21/008* (2013.01); *A61F 9/08*
(2013.01); *A61H 2003/063* (2013.01); *A61H*
*2201/501* (2013.01); *A61H 2201/5012*
(2013.01); *A61H 2201/5064* (2013.01); *A61H*
*2201/5092* (2013.01); *A61H 2201/5097*
(2013.01)

(56) References Cited

U.S. PATENT DOCUMENTS

| | | | |
|---|---|---|---|
| 8,180,396 | B2 | 5/2012 | Athsani et al. |
| 2002/0149681 | A1* | 10/2002 | Kahn .................. G01S 3/7864 348/211.99 |
| 2003/0197612 | A1* | 10/2003 | Tanaka et al. ............. 340/572.1 |
| 2004/0068368 | A1* | 4/2004 | Adams et al. ................ 701/209 |
| 2004/0155815 | A1* | 8/2004 | Muncaster et al. ...... 342/357.09 |
| 2004/0178894 | A1* | 9/2004 | Janssen .......................... 340/435 |
| 2005/0099307 | A1 | 5/2005 | Gilfix et al. |
| 2005/0113075 | A1 | 5/2005 | Haberman et al. |
| 2006/0108426 | A1 | 5/2006 | Hopkins |
| 2006/0129308 | A1 | 6/2006 | Kates |
| 2006/0226973 | A1 | 10/2006 | Catlin |
| 2007/0125442 | A1* | 6/2007 | Tribble .................. A61J 3/002 141/27 |
| 2009/0102859 | A1 | 4/2009 | Athsani et al. |
| 2009/0285445 | A1* | 11/2009 | Vasa .............................. 382/100 |
| 2011/0210167 | A1* | 9/2011 | Lyon .................. G06F 13/4095 235/375 |
| 2011/0216179 | A1 | 9/2011 | Dialameh et al. |

FOREIGN PATENT DOCUMENTS

| | | |
|---|---|---|
| WO | 2006/045819 | 5/2006 |
| WO | 2009/001991 | 12/2008 |
| WO | 2011/144799 | 11/2011 |
| WO | 2012/015579 | 2/2012 |

OTHER PUBLICATIONS

GB Search Report, GB1209585.7, Sep. 17, 2013, 2 pages.
Marzia, "Augmented Reality and iPhone Applications: Narration, Mobile Devices and Urban Space", 2011.
Mpitziopoulos et al., "Hazard Monitoring for Visually Impaired People Enabled by Wireless Sensor Networking Technology", 2008, 7 pages.
"Roberts, ""RFID Technology makes Navigation More Accessible"", Aug. 2011, 2 pages.http://www.blindgadget.com/rfid-techno0logy-makes-navigation-more-accessible".
Su, "Considering Mobile Devices, Context Awareness, and Mobile Users", 2010.
Willis et al., "RFID Information Grid for Blind Navigation and Wayfinding", Proc. of the 2005 Ninth IEEE Intl Symposium on Wearable Computers, 2005, pp. 34-37.
Office Action, dated May 5, 2015, regarding U.S. Appl. No. 14/045,337, 23 pages.
Final Office Action, dated Aug. 21, 2015, regarding U.S. Appl. No. 14/045,337, 24 pages.
Office Action, dated Apr. 4, 2016, regarding U.S. Appl. No. 14/045,337, 57 pages.
Final Office Action, dated Sep. 8, 2016, regarding U.S. Appl. No. 14/045,337, 29 pages.

\* cited by examiner

PROVIDING LOCATION AND SPATIAL DATA ABOUT THE PHYSICAL ENVIRONMENT

CROSS REFERENCE TO RELATED APPLICATIONS

This Application claims the benefit of priority to United Kingdom Patent Application Serial No. 1209585.7, filed on May 30, 2012, the contents of which are hereby incorporated by reference.

FIELD OF INVENTION

This invention relates to the field of providing location and spatial data about the physical environment. In particular, the invention relates to providing location and spatial data about the physical environment to aid the visually impaired.

BACKGROUND OF INVENTION

Signage in the physical environment may indicate specific hazards to specific groups. For example, edge of stair markings or braille signage may be provided for the visually impaired. However, such signage is often not viewable until the user is already very close. Also, such signs are generally shallow in terms of information exchange.

In addition, other hazard indicating signs are lacking in specific detail. For example, a sign may indicate an electrical hazard at the entrance to a space, but this does not give any detail on the exact location or nature of the hazard.

Machine readable symbols with data encoding already exist in many fields. For example, bar codes, or data matrix symbols for mobile phones. However, explicit action is usually required by the user to interpret and act on the symbols.

Therefore, there is a need in the art to address the aforementioned problems.

BRIEF SUMMARY OF THE INVENTION

According to a first aspect of the present invention there is provided a method for providing location and spatial data about the physical environment, comprising: sensing a tag provided in the environment by a mobile device; receiving data from the tag at the mobile device, the data including location and spatial data relating to the physical environment of the tag; and representing the location and spatial data from the tag by the mobile device.

According to a second aspect of the present invention there is provided a system for providing location and spatial data about the physical environment, in the form of a mobile device including: a sensing component for sensing a tag provided in the environment by a mobile device; a tag data receiver for receiving data from the tag at the mobile device, the data including location and spatial data relating to the physical environment of the tag; and a data representing component for representing the location and spatial data from the tag by the mobile device.

According to a third aspect of the present invention there is provided a computer program product for providing location and spatial data about the physical environment, the computer program product comprising a computer readable storage medium having computer-readable program code embodied therewith, the computer-readable program code configures to: sense a tag provided in the environment by a mobile device; receive data from the tag at the mobile device, the data including location and spatial data relating to the physical environment of the tag; and represent the location and spatial data from the tag by the mobile device.

According to a fourth aspect of the present invention there is provided a method substantially as described with reference to the figures.

According to an fifth aspect of the present invention there is provided a system substantially as described with reference to the figures.

The described aspects of the invention provide the advantage of providing spatial and locational information for a location via a mobile device.

BRIEF DESCRIPTION OF THE DRAWINGS

The subject matter regarded as the invention is particularly pointed out and distinctly claimed in the concluding portion of the specification. The invention, both as to organization and method of operation, together with objects, features, and advantages thereof, may best be understood by reference to the following detailed description when read with the accompanying drawings.

Preferred embodiments of the present invention will now be described, by way of example only, with reference to the following drawings in which.

DETAILED DESCRIPTION OF THE DRAWINGS

Figure 1:
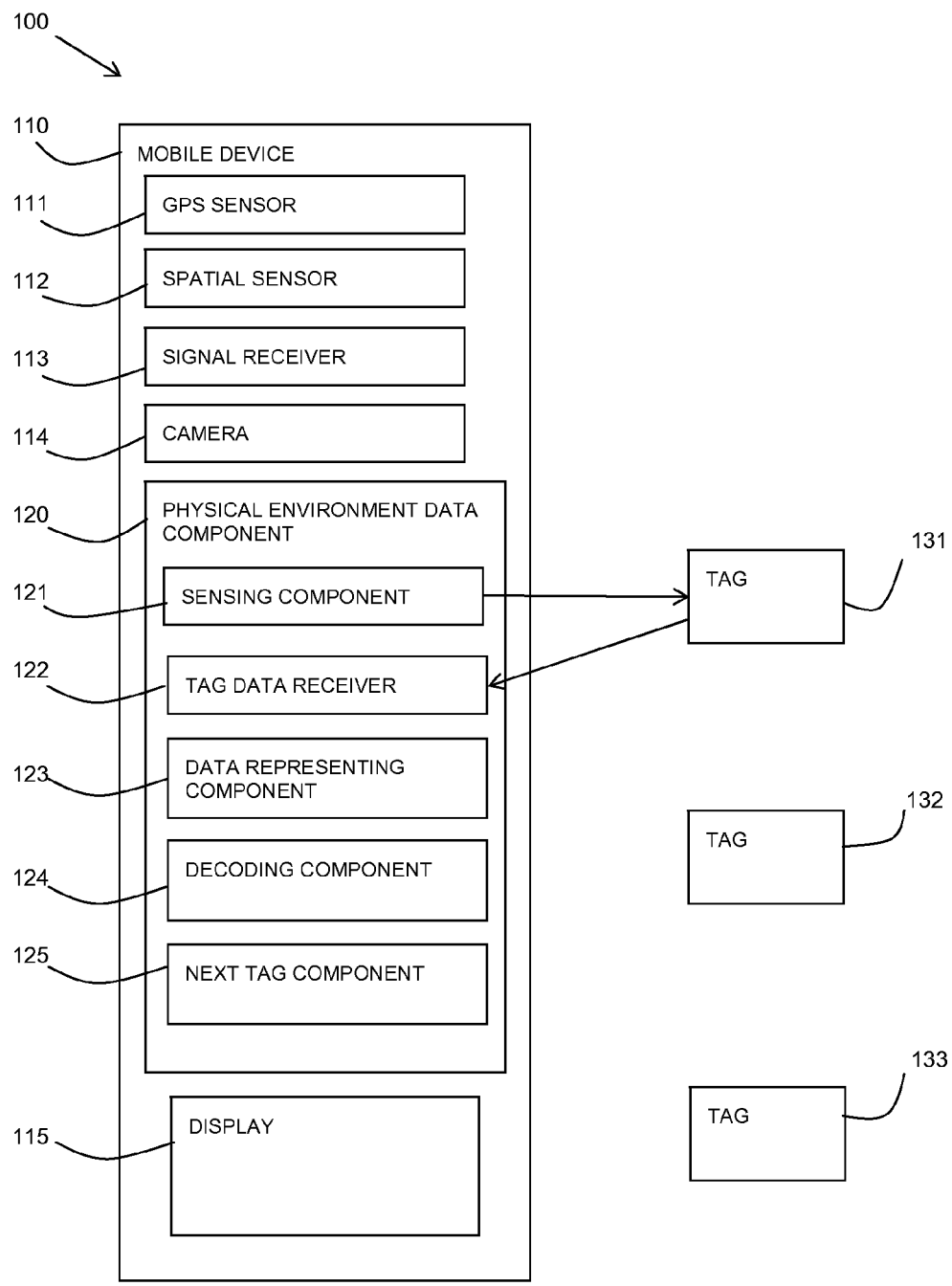
FIG. 1 is block diagram of an example embodiment of a system in accordance with the present invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numbers may be repeated among the figures to indicate corresponding or analogous features.

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Method and system are provided for encoding locational and spatial data about the physical environment in "tags" from which the information may be retrieved by a mobile device and the information may be represented to the user of the mobile device in a suitable manner, such as via auditory information, tactile information, or augmented reality techniques.

Locational and spatial data about the physical environment may be provided by tags, for example, in the form of machine readable symbols or low power local transmitters, with the information to be represented to a user through augmented sensory feedback using a mobile device. For example, trip hazards could be encoded so that a visually-impaired person approaching would be warned via sound or touch or augmented reality techniques, including augmented reality overlay on real time video.

The form of the locational information may be an exact encoded location of the object to which the tag refers. This could be in the form of Global Positioning System (GPS) positional data for locations where GPS can be used. For indoor locations, this may be a triangulation position dependent on the particular Indoor Positioning System (IPS) being used.

The form of the spatial data may be encoded data about the actual object to which the tag refers. This may be the dimensions in 3D, and other data relevant to the particular object.

For a set of stairs for example, this might include the number of stairs and their depth and orientation in space. For a barrier, for example, a fence or wall, this could include the height and thickness.

The data may be presented in a variety of ways, including an auditory signal alert as the user approaches the location, haptic type vibrating alerts used in the same way, tool tip type overlays over the real time video containing additional information as text, 3D wire-frame overlays showing the shape and location of the information.

As an example, tool tip type overlays may appear over the video as the user approaches a set of stairs. The stairs may be identified in the video frame with a wire frame overlay. This overlay could be 'clickable', which would trigger further text information about the hazard to appear, or to allow the user to zoom in on the area to view it in more detail before navigating it.

Referring to FIG. 1, a block diagram shows an example embodiment of the described system.

A mobile device 110 may be provided, for example, in the form of a mobile computing device such as a tablet or a mobile telephone device. The mobile device 110 may include all or some of the components of: GPS sensor 111, spatial sensor 112, signal receiver 113, camera 114, and display 115, etc.

In the described system, the mobile device 110 includes a physical environment data component 120 which provides location and spatial data about the physical environment to the mobile device 110 user.

The physical environment data component 120 may include a sensor component 121 for sensing a tag and a tag data receiver 122 for receiving and decoding data provided by tags 131-133 at physical locations which provide location and spatial data about the physical environment at the physical location of the tag 131-133. For example, tags 131-133 may be provided at physical hazards, potentially dangerous places, or places of interest. A tag 131-133 in a close location to the mobile device 110 may be sensed and the tag data received by the tag data receiver 122.

The physical environment data component 120 may also include data representing component 123 for representing the received tag data to the user of the mobile device 110. The tag data may be represented via audio, tactile, or using augmented reality techniques.

The physical environment data component 120 may also include a decoding component 124 for decoding location and spatial data received from a tag 131-133.

The physical environment data component 120 may also include a next tag component 125 for determining the location of a next tag 131-133 from the data supplied by a tag 131-133. The data may provide directions to the next tag 131-133.

The tag data receiver 121 may include a video camera which senses the tags 131-133 and augments the video image display in real time.

A first embodiment of a system is described in which machine readable visual symbols encoding spatial and locational information about the physical environment are provided. Such spatial and locational information may augment existing physical signs, and can be automatically identified and decoded by a video camera in a mobile device, which may then represent this data to a user in various ways in real time.

Figure 2:
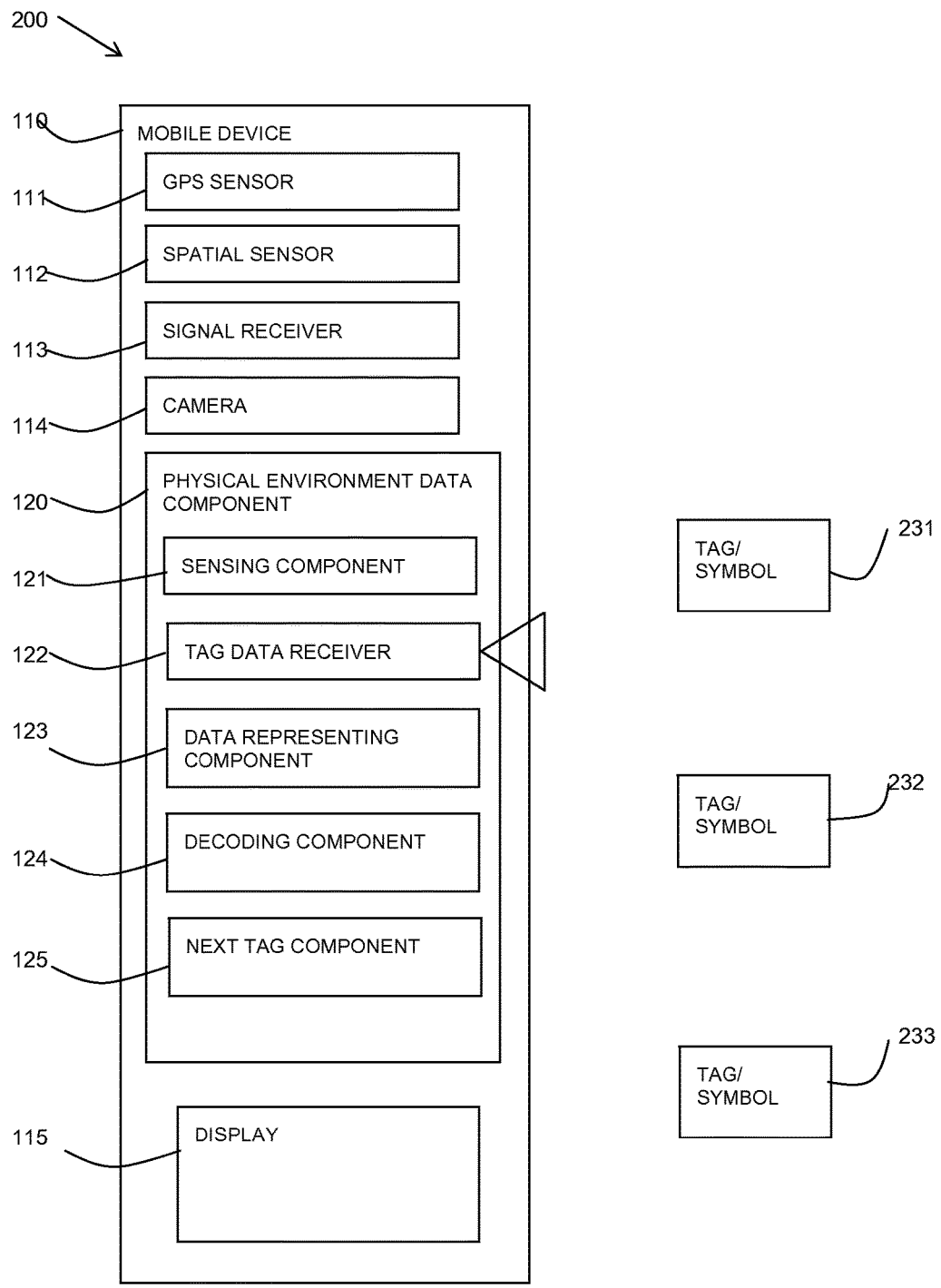
FIG. 2 is block diagram of an example embodiment of a system in accordance with the present invention.

An example of the first embodiment is shown in FIG. 2. FIG. 2 shows the system 200 of FIG. 1 with the tags 231-233 in the form of machine readable visual symbols which may be read by the tag data receiver 121 of the mobile device 110. In this embodiment, the tag data receiver 121 may be a still or video camera for receiving the image of the symbol of the tags 231-233.

When using visual tags, the tags 231-233 may be identified by the camera using video analytics. This would work in a similar way to Quick Response (QR) tags. These may be of a size large enough to be identified using the video camera viewing the space.

Alternatively, tags 231-233 may be initially identified in the space using a primary tag, which can then trigger the video camera to zoom in to gather further details. A primary tag may take the form of an easily identifiable surround which can be seen at longer distances, which signifies that a tag 231-233 is present within it. For example, this could be a brightly colored sign edge. A video camera application may pick this up, and then may zoom to view the tag 231-233 and capture the information encoded in it.

Many applications already exist to recognize real world elements using mobile devices and display additional data overlaid to the user. For example, The Layar Reality Browser (Layar is a trade mark of Layar) provides an augmented reality platform for web services serving geo-located points of interest in the vicinity of the user. Image detection and identification on mobile devices are also known in the art.

A second embodiment of a system is described in which low cost, low power wireless transmitters encoding and broadcasting spatial and locational information about the physical environment are provided. Such spatial and locational information may augment existing physical signs, and can be automatically identified and decoded by a mobile devices equipped with the appropriate receivers, which may then re-present this data to a user in various ways in real time.

Figure 3:
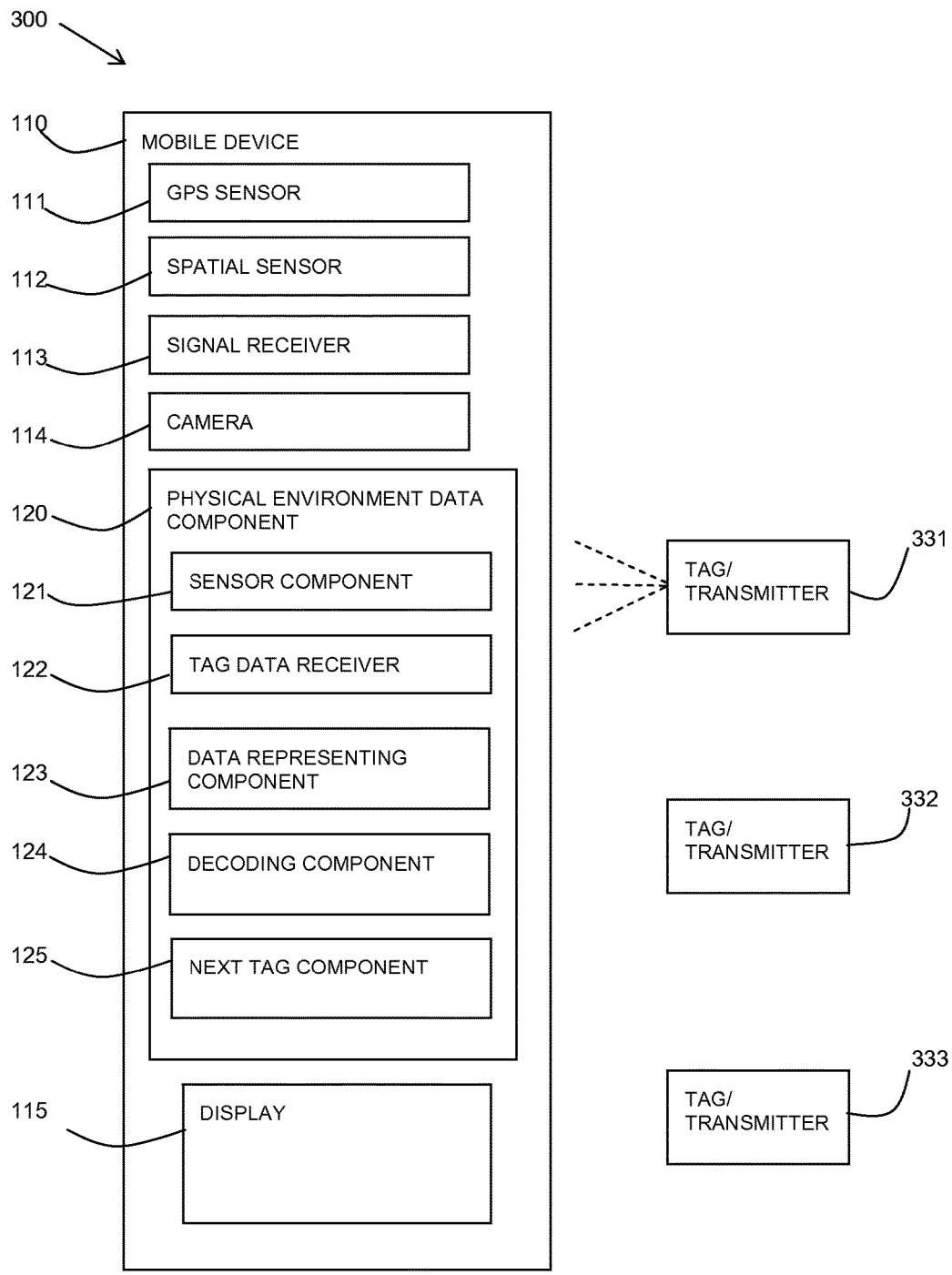
FIG. 3 is block diagram of an example embodiment of a system in accordance with the present invention.

An example of the second embodiment is shown in FIG. 3. FIG. 3 shows the system 300 of FIG. 1 with the tags 331-333 in the form of transmitters whose signal may be received by the tag data receiver 121 of the mobile device 110. In this embodiment, the tag data receiver 121 may be a radio signal receiver. In this embodiment, the tag data receiver 121 may include both a signal receiver and a camera for receiving an image of the location of the tags 331-333 as well as their data.

Transmitters may take the form of low power, low cost wireless devices, using protocols such as Radio-frequency identification (RFID), Bluetooth (proprietary open wireless technology) or ZigBee (a wireless mesh network standard, ZigBee is a trade mark of ZigBee Alliance). Transmitters may also encode the location of other transmitters, enabling a chain of communication throughout a physical space. A mobile device, viewing the environment through a video camera, may identify or sense and decode transmitters in its field of reception, then decode and represent the data to the user in a variety of ways.

A physical space may be 'tagged' with wireless transmitters or machine readable symbols sited at areas of potential hazard or interest, replacing or augmenting traditional signage. For example, a set of stairs may be tagged and would contain encoded data giving the exact location and physical dimensions of the steps.

Once the environment is "tagged" in this way, a mobile device viewing the environment through a video camera would identify and decode the symbols in its field of view using visual analytics, and then decode and re-present the data to the user in a variety of ways.

In some situations (for example, a busy indoor location), a combination of the visual and broadcast tags may be used. This may be required to ensure that all tags are read by the application, dependent on the orientation of possible signage. Many public spaces, for example, museums or galleries have fairly defined flow patterns for visitors so it is relatively easy to site signage where it can be seen from many different positions Emerging tablets, mobile telephones, and other mobile devices are now fitted often with highly accurate spatial and locational sensors, broadcast signal receivers, and high-resolution cameras. These technologies are rapidly improving in resolution, and the devices themselves rapidly increasing in processing power, so true visual analytics using mobile devices in real time video is possible.

Figure 4:
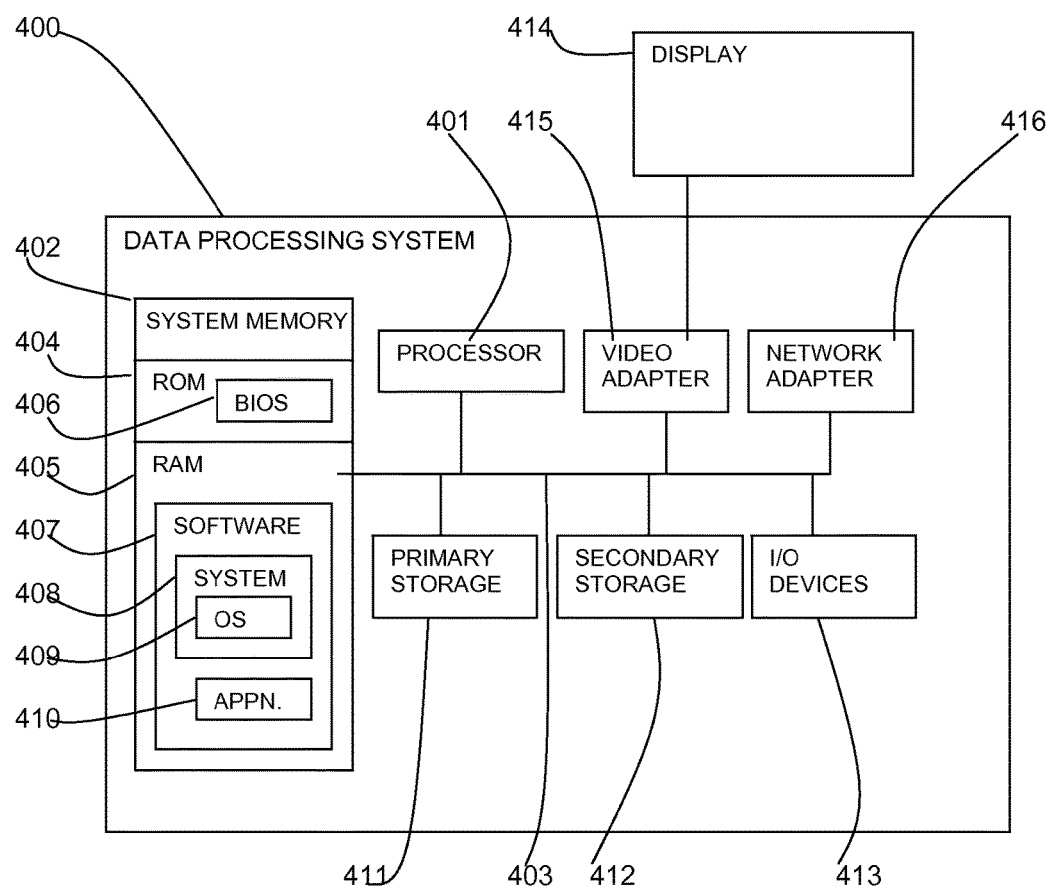
FIG. 4 is a block diagram of an embodiment of a computer system in which the present invention may be implemented.

Referring to FIG. 4, an exemplary system for the mobile device includes a data processing system 400 suitable for storing and/or executing program code including at least one processor 401 coupled directly or indirectly to memory elements through a bus system 403. The memory elements may include local memory employed during actual execution of the program code, bulk storage, and cache memories which provide temporary storage of at least some program code in order to reduce the number of times code must be retrieved from bulk storage during execution.

The memory elements may include system memory 402 in the form of read only memory (ROM) 404 and random access memory (RAM) 405. A basic input/output system (BIOS) 406 may be stored in ROM 404. System software 407 may be stored in RAM 405 including operating system software 408. Software applications 410 may also be stored in RAM 405.

The system 400 may also include a primary storage means 411 such as a magnetic hard disk drive and secondary storage means 412 such as a magnetic disc drive and an optical disc drive. The drives and their associated computer-readable media provide non-volatile storage of computer-executable instructions, data structures, program modules and other data for the system 400. Software applications may be stored on the primary and secondary storage means 411, 412 as well as the system memory 402.

The computing system 400 may operate in a networked environment using logical connections to one or more remote computers via a network adapter 416.

Input/output devices 413 may be coupled to the system either directly or through intervening I/O controllers. A user may enter commands and information into the system 400 through input devices such as a keyboard, pointing device, or other input devices (for example, microphone, joy stick, game pad, satellite dish, scanner, or the like). Output devices may include speakers, printers, etc. A display device 414 is also connected to system bus 403 via an interface, such as video adapter 415.

Figure 5:
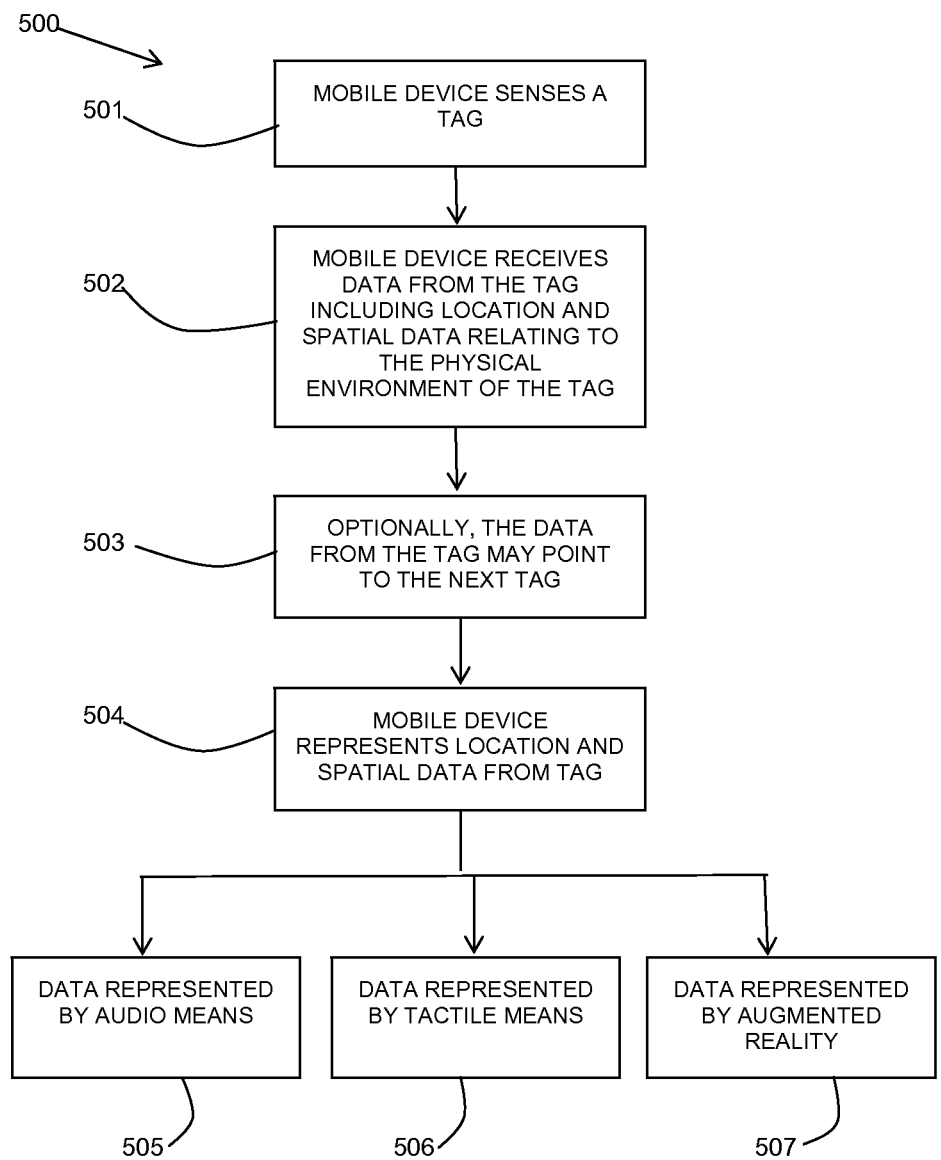
FIGS. 5 to 8 are flow diagrams of example embodiments of aspects of a method in accordance with the present invention.

Referring to FIG. 5, a flow diagram 500 shows an embodiment of the described method. A mobile device, such as a mobile computing device or phone, may sense 501 a tag. For example, the tag may be a transmitting device or a machine-readable symbol. The mobile device may receive 502 data from the tag including location and spatial data relating to the physical environment of the tag.

Optionally, the data received from the tag may point 503 or provide information regarding the location of the next tag.

The mobile device may represent 504 the location and spatial data from the tag in a manner suitable for the user. For example, the user may be visually impaired in which case the data may be represented by audio means 505 or by tactile means 506 or by augmented reality 507.

Figure 6:
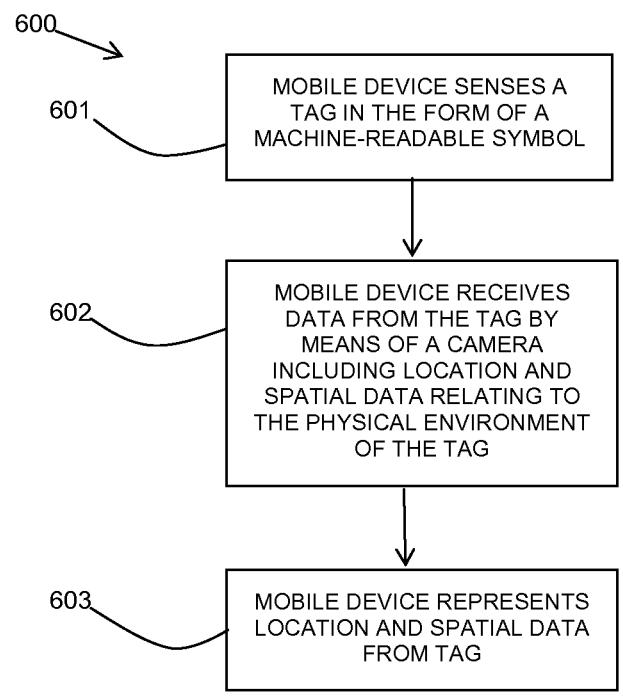

Referring to FIG. 6, a flow diagram 600 shows an example embodiment of the described method in which the tags are machine-readable symbols.

The mobile device may sense 601 a tag in the form of a machine-readable symbol. The mobile device may receive 602 data from the tag by means of a camera including location and spatial data relating to the physical environment of the tag.

The mobile device may represent 603 the location and spatial data from the tag for the user.

Figure 7:
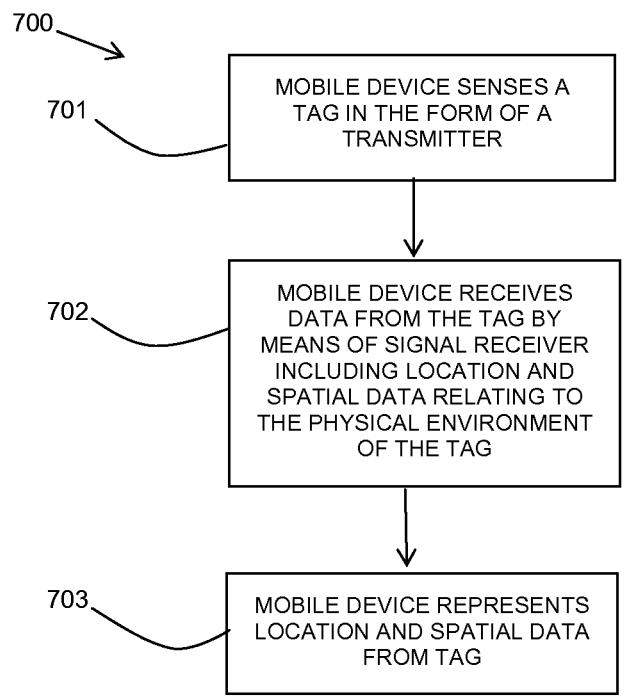

Referring to FIG. 7, a flow diagram 700 shows an example embodiment of the described method in which the tags are transmitting devices.

The mobile device may sense 701 a tag in the form of a transmitting device when the mobile device is in the transmission range of the transmitter. The mobile device may receive 702 data from the tag by means of a signal receiver including location and spatial data relating to the physical environment of the tag.

The mobile device may represent 703 the location and spatial data from the tag for the user.

Figure 8:
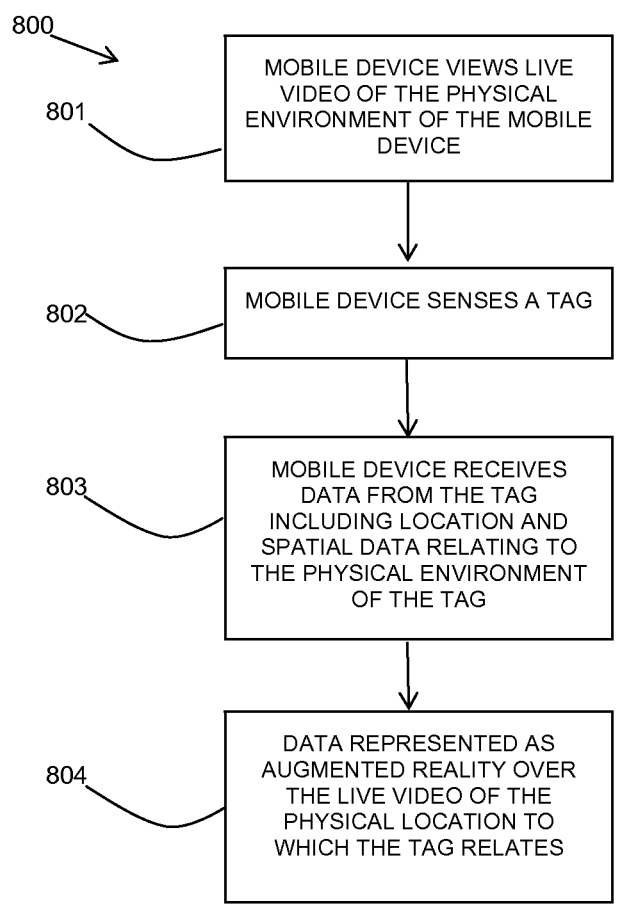

Referring to FIG. 8, a flow diagram 800 shows an example embodiment of the described method in which a mobile device views 801 live video of the physical environment of the mobile device.

The mobile device may sense 802 a tag and may receive 803 data from the tag including location and spatial data relating to the physical environment of the tag.

The mobile device may represent 804 the location and spatial data from the tag as augmented reality over the live video of the physical location to which the tag relates.

Before navigating through the space, a user could "view" a scene using the mobile device, and access detailed information about all of the potential hazards in that space, and use the device to access real time feedback as a video overlay, audio commentary, or tactile feedback indicating their proximity to such hazards, by using the locational and positional sensors in the device.

For example, a visually impaired user may have some close vision, but lack detail in depth vision at any other depth. Using such a system, the user could view the space, and the mobile device would present all the hazards appropriate to them as an augmented reality overlay over the real time video, allowing zooming in to more closely examine the space before attempting to navigate.

Another example would be adding such transmitters to signage indicating chemical or explosive risk. Whilst these signs indicate danger, they do not signal in any detail the type or exact location of the hazard. Emergency services entering a space could use a mobile device to access transmitted signals or "scan" such signage, and access data indicating the exact nature, amount and physical location of the hazard.

The invention can take the form of an entirely hardware embodiment, an entirely software embodiment or an embodiment containing both hardware and software elements. In a preferred embodiment, the invention is implemented in software, which includes but is not limited to firmware, resident software, microcode, etc.

The invention can take the form of a computer program product accessible from a computer-usable or computer-readable medium providing program code for use by or in connection with a computer or any instruction execution system. For the purposes of this description, a computer usable or computer readable medium can be any apparatus that can contain, store, communicate, propagate, or transport the program for use by or in connection with the instruction execution system, apparatus or device.

The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read only memory (ROM), a rigid magnetic disk and an optical disk. Current examples of optical disks include compact disk read only memory (CD-ROM), compact disk read/write (CD-R/W), and DVD.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system". Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

Improvements and modifications can be made to the foregoing without departing from the scope of the present invention.

The invention claimed is:

1. A system for providing location and spatial data about a physical environment, in a form of a mobile device comprising:
    a sensing component configured to sense a tag provided in the physical environment by a mobile device, wherein the sensing component is configured to sense a symbol tag in a form of a machine-readable visual symbol encoding the location and spatial data about the physical environment and sense a signal tag in a form of a transmitter device;
    a tag data receiver configured to receive data from the tag at the mobile device, the data including location and spatial data about the physical environment of the tag, wherein the tag data receiver is configured to receive the data from the tag by processing an image of the machine-readable visual symbol by the mobile device and receive the data from the tag by receiving a signal by the mobile device, wherein the tag data receiver includes a camera configured to identify a location of the tag by processing the image of the machine-readable visual symbol and a signal receiver configured to receive data about a hazard in the physical environment from the tag by receiving the signal; and
    a data representing component configured to represent the location and spatial data from the tag by the mobile device.

2. The system as claimed in claim 1, further comprising: multiple tags provided in the physical environment that are each configured to provide location and spatial data about the physical environment, wherein the spatial data identifies physical dimensions of an object in the physical environment.

3. The system as claimed in claim 1, further comprising:
    a decoding component configured to decode the data received from the tag to retrieve the location and spatial data.

4. A system for providing location and spatial data about a physical environment, in a form of a mobile device comprising:
    a sensing component configured to sense a tag provided in the physical environment by a mobile device;
    a tag data receiver configured to receive data from the tag at the mobile device, the data including location and spatial data about the physical environment of the tag, wherein the tag data receiver includes a camera configured to identify a location of the tag by processing the image of the machine-readable visual symbol and a signal receiver configured to receive data about a hazard in the physical environment from the tag by receiving the signal;
    a data representing component configured to represent the location and spatial data from the tag by the mobile device; and
    a next tag component configured to determine, from the data received from the tag, a location of another tag configured to provide location and spatial data defining a physical environment of the another tag.

5. The system as claimed in claim 1, wherein the data representing component is configured to represent the data by audio means.

6. The system as claimed in claim 1, wherein the data representing component is configured to represent the data by tactile means.

7. The system as claimed in claim 1, wherein the data representing component is configured to represent the data by augmented reality means with the location and spatial information overlain over the live video as textual information.

8. The system as claimed in claim 1, wherein the tag data receiver includes a camera for viewing a live video of the physical environment of the mobile device; and
    wherein the data representing component is configured to represent the location and spatial data by augmented reality over a view of the live video.

9. The system as claimed in claim 1, wherein the tag data receiver includes a camera for viewing a live video of a physical environment of the mobile device, wherein the camera is configured to zoom in to gather further details of the tag responsive to the tag being sensed by the sensing component.

10. The system as claimed in claim 1, wherein the mobile device is a mobile phone.

11. The system as claimed in claim 1, wherein processing the image of the machine-readable visual symbol comprises ascertaining the location and spatial data about the physical environment defined by the machine-readable visual symbol.

12. The system as claimed in claim 4, wherein the processing the image of the visual symbol comprises ascertaining the location and spatial data about the physical environment defined by the visual symbol.

* * * * *